United States Patent [19]
Kwantes

[11] 3,972,950
[45] Aug. 3, 1976

[54] PROCESS FOR THE PURIFICATION OF BISPHENOL A

[75] Inventor: Arien Kwantes, Amsterdam, Netherlands

[73] Assignee: Shell Oil Company, Houston, Tex.

[22] Filed: May 7, 1975

[21] Appl. No.: 575,277

[30] Foreign Application Priority Data
Aug. 14, 1974 Netherlands .................. 7410872

[52] U.S. Cl. .................................. 260/619 A
[51] Int. Cl.² ................................ C07C 37/22
[58] Field of Search ............... 260/619 R, 619 A

[56] References Cited
UNITED STATES PATENTS

| | | | |
|---|---|---|---|
| 2,959,622 | 11/1960 | Gimme et al. | 260/619 A |
| 3,207,795 | 9/1965 | Prahl et al. | 260/619 A |
| 3,290,391 | 12/1966 | Prahl et al. | 260/619 A |
| 3,326,986 | 6/1967 | Dugan et al. | 260/619 A |
| 3,493,622 | 2/1970 | Ornsten et al. | 260/619 A |
| 3,535,389 | 10/1970 | DeJong | 260/619 A |

*Primary Examiner*—Norman Morgenstern

[57] ABSTRACT

Crude 2,2-bis(4-hydroxyphenyl)propane containing impurities such as 2-(2-hydroxyphenyl)-2-(4-hydroxyphenyl)propane is purified by first dissolving the crude material in a polyhydroxy solvent then adding water and an ether having a boiling point less than 110°C whereby the ether extracts the 2,2-bis(4-hydroxyphenyl)propane. The ether-2,2-bis(4-hydroxyphenyl)propane extract is then distilled in the presence of toluene wherein the toluene-2,2-bis(4-hydroxyphenyl)propane bottoms product is separated and cooled to form a purified 2,2-bis(4-hydroxyphenyl)propane precipitate which is subsequently recovered.

5 Claims, No Drawings

PROCESS FOR THE PURIFICATION OF BISPHENOL A

BACKGROUND OF THE INVENTION

The compound 2,2-bis(4-hydroxyphenyl)propane, also called para, para-diphenylolpropane or Bisphenol A, is generally prepared by reacting phenol and acetone in the presence of an acidic catalyst such as hydrochloric acid along with a sulfur compound such as methyl mercaptan which acts as a co-catalyst. This method of preparing 2,2-bis(4-hydroxyphenyl)propane is disclosed in U.S. Pat. No. 2,730,552. However, the reaction between phenol and acetone to form 2,2-bis(4-hydroxyphenyl)propane also forms a number of byproducts including 2-(2-hydroxyphenyl)-2-(4-hydroxyphenyl)propane also called ortho, para-diphenylolpropane, which is an isomer of 2,2-bis(4-hydroxyphenyl)propane. Further typical impurities include 2,2-bis(2-hydroxyphenyl)propane, higher condensation products such as trisphenols (condensation products of three moles of phenol and two moles of acetone) and chroman derivatives (internal condensation products of two moles of phenol and two moles of acetone), plus still higher condensation products in the form of resins and tars. As stated herein, "diphenylolpropane-type compounds" and "crude 2,2-bis(4-hydroxyphenyl)propane" refer to 2,2-bis(4-hydroxyphenyl)propane and the by-product derivatives indicated above.

In certain commercial applications of 2,2-bis(4-hydroxyphenyl)propane, such as in the production of polycarbonates, the 2,2-bis(4-hydroxyphenyl)propane must be of high purity, generally containing less than 0.3% weight impurities. Therefore, a number of methods to isolate 2,2-bis(4-hydroxyphenyl)propane in a substantially pure state have already been proposed.

One purification method, taught in East German Patent Specification 54,374, involves the crystallization of 2,2-bis(4-hydroxyphenyl)propane from a methanol solution by the addition of water or by the addition of halo-hydrocarbons, preferably dichloroethane, plus water, followed by washing the crystals with similar halohydrocarbons. However, this method is not attractive since it calls for the additional step of washing the crystals with halohydrocarbons.

Other relatively more simple recrystallization and extraction methods such as the method taught in U.S. Pat. No. 3,326,986 are known in the art. However, if these techniques are used to obtain 2,2-bis(4-hydroxyphenyl)propane in high purity, a number of operations, such as washing and flashing off solvent and/or wash liquid must be performed, which is a disadvantage, especially if 2,2-bis(4-hydroxyphenyl)propane is to be purified in large amounts.

Still further purification methods comprise recrystallizing the 2,2-bis(4-hydroxyphenol)propane from a suitable solvent such as benzene, toluene and methylene chloride as disclosed in British Patent 891,800 or diisopropyl ether as disclosed in British Patent 794,476.

Another purification method is taught in co-pending U.S. Ser. No. 511,980, filed Oct. 3, 1974, now U.S. Pat. No. 3,919,330 wherein 2,2-bis(4-hydroxyphenyl)propane is recovered from diphenylolpropane-type compounds by dissolving the diphenylolpropane-type compounds in ethylene glycol and adding a specified quantity of water to the ethylene glycol solution to precipitate the 2,2-bis(4-hydroxyphenyl)propane which is subsequently recovered by filtration or centrifugation. Although this method produces relatively high purity 2,2bis(4-hydroxyphenyl)propane it has been found that to obtain even higher purity 2,2-bis(4-hydroxyphenyl)propane it is necessary to subject the precipitated product to a subsequent crystallization, preferably from a toluene solution. When higher purity 2,2-bis(4-hydroxyphenyl)propane is necessary it would be desirable to restrict the handling of solid matter to one crystallization instead of two crystallizations.

SUMMARY OF THE INVENTION

The invention relates to a process for the purification of 2,2-bis(4-hydroxyphenyl)propane in which 2,2-bis(4-hydroxyphenyl)propane containing impurities such as 2-(2-hydroxyphenyl)-2-(4-hydroxyphenyl)propane is first dissolved in a polyhydric solvent, then water and an ether having a boiling point below 110°C are added, the ether extracting the purified 2,2-bis(4-hydroxyphenyl)propane. Next the ether-2,2-bis(4-hydroxyphenyl)propane extract is separated. The ether-2,2-bis(4-hydroxyphenyl)propane extract is then distilled in the presence of toluene, the toluene-2,2-bis(4-hydroxyphenyl)propane bottoms product is separated, and the purified 2,2-bis(4-hydroxyphenyl)propane is precipitated from the cooled toluene-2,2-bis(4-hydroxyphenyl)propane bottoms product.

DETAILED DESCRIPTION OF THE INVENTION

It has been found that very pure 2,2-bis(4-hydroxyphenyl)propane (greater than 99% purity) is obtained in high yields by use of the purification method according to the present invention. The purification procedure comprises:

a. dissolving the crude 2,2-bis(4-hydroxyphenyl)propane and impurities in a polyhydroxy solvent;

b. contacting the polyhydroxy solvent-crude 2,2-bis(4-hydroxyphenyl)propane solution with water and an ether, said ether having a boiling point less than 110°C, wherein said ether extracts the 2,2-bis(4-hydroxyphenyl)propane;

c. separating the ether-2,2-bis(4-hydroxyphenyl)propane extract;

d. distilling the ether-2,2-bis(4-hydroxyphenyl)propane extract in a column and in the presence of toluene and recovering as bottoms product a toluene-2,2-bis(4-hydroxyphenyl)propane solution;

e. cooling the toluene-2,2-bis(4-hydroxyphenyl)propane bottoms product to form a purified 2,2-bis(4-hydroxyphenyl)propane precipitate; and f. recovering the purified 2,2-bis(4-hydroxyphenyl)propane.

The crude 2,2-bis(4-hydroxyphenyl)propane to be purified is prepared by a variety of methods, such as the method described in U.S. Pat. No. 2,730,552. In one preferred procedure, taught in co-pending U.S. Ser. No. 432,376, filed Jan. 10, 1974, 2,2-dimethyl-1,3-dioxolane and phenol are reacted to form 2,2-bis(4-hydroxyphenyl)propane while ethylene glycol is produced as a by-product. Therefore, when 2,2-bis(4-hydroxyphenyl)propane is produced according to the invention disclosed in U.S. Ser. No. 432,376, one of the solvents to be used in the purification stage and the crude product to be purified are produced in a single step, thereby greatly increasing the efficiency and utility of the invention as is shown below.

The crude 2,2-bis(4-hydroxyphenyl)propane to be purified should contain as a minimum 80% and preferably at least 90% by weight 2,2-bis(4-hydroxyphenyl)propane calculated on the total amount of diphenylolpropane-type compounds present. However, the purification of lower quality crude 2,2-bis(4-hydroxyphenyl)propane can also be accomplished.

Suitable polyhydroxy solvents for use in this invention include alkane diols, such as ethylene glycol, propane diol, and the butane diols, and alkane triols such as glycerol. A preferred polyhydroxy solvent is ethylene glycol.

The ratio of crude 2,2-bis(4-hydroxyphenyl)propane to polyhydroxy solvent to be employed is not critical. Suitable weight ratios of polyhydroxy solvent to crude 2,2-bis(4-hydroxyphenyl)propane are from about 98:2 to about 20:80. Preferred weight ratios are between about 80:20 and about 75:25 polyhydroxy solvent to crude 2,2-bis(4-hydroxyphenyl)propane.

It is important that the crude 2,2-bis(4-hydroxyphenyl)propane to be purified and the polyhydroxy solvent employed be substantially free of phenol, since otherwise the phenol adduct of 2,2-bis(4-hydroxyphenyl)propane interferes with the purification process. "Substantially free of phenol" means that the total amount of phenol present not exceed 10% weight based on the amount of polyhydroxy solvent employed. Preferably less than 1% phenol is present.

The ether to be employed in the invention should be at least substantially immiscible with water, whereas the purified 2,2-bis(4-hydroxyphenyl)propane readily dissolves in the ether. The main impurity normally present in crude 2,2-bis(4-hydroxyphenyl)propane, namely 2-(2-hydroxyphenyl)-2-(4-hydroxyphenyl)propane, is highly soluble in the aqueous polyhydroxy solvent solution.

After the transfer of the 2,2-bis(4-hydroxyphenyl)propane from the polyhydroxy solvent to the ether solvent, purification with toluene takes place. For this toluene purification to proceed satisfactorily, the ether employed must have a boiling point less than the boiling point of toluene, that is, the ether must have a boiling point less than 100°C. Suitable ethers include diethyl ether, ethyl-n-propyl ether, ethylisopropyl ether, methylisopropyl ether, methyl-tert-butyl ether, di-n-propyl ether, diisopropyl ether, and cyclic ethers such as furan. A preferred ether is diisopropyl ether.

The quantity of ether employed is not critical. The minimum amount of ether employed is usually that amount needed to transfer the 2,2-bis(4-hydroxyphenyl)propane from the polyhydroxy solvent to the toluene solvent without the formation of a precipitate. The use of very large quantities of ether has obvious technical disadvantages. Typically the weight ratio of ether to 2,2-bis(4-hydroxyphenyl)propane is between about 1:5 and about 10:1, preferably between about 1:1 and about 4:1.

For satisfactory results, the weight ratio of water to polyhydroxy solvent is between about 40:60 and about 90:10, preferably about 50:50.

The contacting of the crude 2,2-bis(4-hydroxyphenyl)propane-polyhydroxy solvent solution with water and ether is carried out in any contacting apparatus suitable for the purpose, such as in a rotating disc contactor (RDC) or in one or more mixer/settler combinations. Preferably the contacting takes place in an RDC with at least two and preferably at least three theoretical trays.

In a preferred embodiment, the solution of diphenylolpropane-type compounds in the polyhydroxy solvent enters the RDC midway up the column, while above and below the inlet point of the solution, water and diisopropyl ether are introduced, respectively, such that the liquid-liquid extraction occurs in a countercurrent fashion. The bottoms stream from the RDC contains very little diisopropyl ether and only trace amounts of 2,2-bis(4-hydroxyphenyl)propane, while the top steam from the RDC comprises a solution of 2,2-bis(4-hydroxyphenyl)propane in diisopropyl ether and only a slight amount of water.

Suitable contacting temperatures vary from about 20°C to the boiling point of the ether employed. Preferred temperatures are between about 30°C and about 50°C. Atmospheric, subatmospheric and superatmospheric pressures are employed. Atmospheric pressures are preferred The residence time of the mixture of crude 2,2-bis(4-hydroxyphenyl)propane and polyhydroxy solvent in the contacting apparatus is not critical. Preferred residence times are between about 10 minutes and about 60 minutes.

The ether-2,2-bis(4-hydroxyphenyl)propane extract solution stream from the contacting apparatus is then contacted with toluene in a suitable process wherein a toluene-2,2-bis(4-hydroxyphenyl)propane solution is recovered. Typically, the solution of 2,2-bis(4-hydroxyphenyl)propane and ether are mixed with toluene, and the resulting solution routed to a distillation column for separation. The ether and any water present are removed as the overhead from the column and are recycled, if desired, to the contacting apparatus. The bottoms stream from the distillation column comprises 2,2-bis(4-hydroxyphenyl)propane, preferably completely dissolved in toluene. If desired the toluene stream is routed directly to the distillation column rather than being premixed with the 2,2-bis(4-hydroxyphenyl)propane solution. The top temperature of the distillation column typically varies from about 40°C to about 70°C, preferably about 65°C. With these top temperatures the bottoms temperatures of the distillation column are typically between about 100°C and about 130°C, preferably about 120°C.

The amount of toluene employed is usually that amount needed to completely dissolve the 2,2-bis(4-hydroxyphenyl)propane so as to avoid the premature formation of precipitates. Typically weight ratios of toluene to 2,2-bis(4-hydroxyphenyl)propane of from about 3:2 to about 5:2 are employed. Larger amounts of toluene are not precluded.

The hot solution of 2,2-bis(4-hydroxyphenyl)propane in toluene is subsequently cooled to obtain a slurry of the 2,2-bis(4-hydroxyphenyl)propane. Typically, the solution of 2,2-bis(4-hydroxyphenyl propane in toluene is cooled to between about 40°C and about 80°C, preferably about 60°C yielding a slurry of high purity 2,2-bis(4-hydroxyphenyl)propane in toluene. Any 2-(2-hydroxyphenyl)-2-(4-hydroxyphenyl)propane present remains in solution due to the higher solubility of 2-(2-hydroxyphenyl)-2-(4-hydroxyphenyl)propane in toluene. The slurry of 2,2-bis(4-hydroxyphenyl)propane obtained is then separated in a manner known in the art, such as with the aid of a rotating drum filter. The filter cake is typically washed at least once with toluene. The crystals of high pruity 2,2-bis(4-hydroxyphenyl)propane are then dried on a conveyor. The mother liquor remaining after the crystals of high purity 2,2-bis(4-hydroxyphenyl)propane are recovered is then distilled to separate toluene. The bottoms product obtained after distillation of the mother liquor contains significant amounts of 2-(2hydroxyphenyl)-2-(-bis(4-hydroxyphenyl)propane, which is an isomer of 2,2-bis(4-hydroxyphenyl)propane, and is preferably recycled to the reactor where the 2,2-bis(4-hydroxyphenyl)propane is prepared. This bottoms stream may also be subjected to an isomerization process to convert the 2-(2-hydroxyphenyl)-2-(4-hydroxyphenyl)propane to 2,2-bis(4-hydroxphenyl)propane.

The following embodiment illustrates the invention. It is to be understood, however, that the Illustrative Embodiment is presented for the purpose of illustration only, and that the invention is not to be regarded as limited to any of the specific materials or reactants recited therein. Note that all parts expressed in the embodiment are parts by weight per hour.

ILLUSTRATIVE EMBODIMENT

One hundred parts of crude 2,2-bis(4-hydroxyphenyl)propane having a weight ratio of 2,2-bis(4-hydroxyphenyl)propane to 2-(2-hydroxyphenyl)-2-(4-hydroxyphenyl)propane of 90.3:9.7 was dissolved in 100 parts of dry ethylene glycol. The resulting solution was introduced midway up an RDC having 3 theoretical trays. The quantity of phenol present in the solution was less than 0.2%w based on the amount of ethylene glycol. At the bottom of the RDC 200 parts of diisopropyl ether were introduced while at the top of the RDC 100 parts of water were introduced. The countercurrent liquid-liquid extraction was conducted at 40°C and atmospheric pressure.

The bottoms stream from the RDC contained 88 parts water, 100 parts ethylene glycol, 1 part diisopropyl ether, and less then 0.02 parts 2,2-bis(4-hydroxyphenyl)propane. The bottoms stream was then subjected to a distillation, after which the water and diisopropyl ether were recycled to the RDC. The ethylene glycol was also reused to dissolve the crude 2,2-bis(4-hydroxyphenyl)propane.

The top stream from the RDC contained 100 parts diphenyolpropane-type compounds, 199 parts diisopropyl ether and 12 parts water. This stream was combined with 200 parts toluene and routed to a distillation column. During the distillation the 2,2-bis(4-hydroxyphenyl)propane present was transferred to the toluene fraction, so that in fact an exchange of solvent had occurred. The distillation took place at a bottoms temperature of about 120°C and a top temperature of between 62°C and 65°C.

The top stream from the distillation column, comprising 11 parts water and 200 parts diisopropyl ether, was recycled to the RDC after phase separation. The bottoms stream from the distillation column comprised a mixture of 100 parts diphenylolpropane-type compounds dissolved in 200 parts toluene. This bottoms stream was then cooled to about 60°C by the boiling of toluene under reflux conditions (0.2 atmosphere). The cooling process yielded a slurry of 2,2-bis(4-hydroxyphenyl)propane crystals in toluene. Due to the higher solubility of 2-(2-hydroxyphenyl)-2-(4-hydroxyphenyl)propane in toluene, no crystals of 2-(2-hydroxyphenyl)-2-(4-hydroxyphenyl)propane were formed under these conditions. The crystal slurry was then filtered at ambient temperature over a rotating drum filter and washed with 200 parts toluene to remove, by means of dilution, as much of the mother liquor from the crystals as possible. A crystal mass was obtained containing 85 parts of purified 2,2-bis(4-hydroxyphenyl)propane (purity 99.4% weight) and 1 part toluene. The remainder of toluene was removed by air drying at 100°C on a conveyor.

The mother liquor obtained during the crystalization, comprising 199 parts toluene, 8 parts 2-(2-hydroxyphenyl)-2-(4-hydroxyphenyl)propane and 5 parts 2,2-bis(4-hydroxyphenyl)propane, was routed to a distillation column were the toluene was removed as the tops stream. The toluene removed was then used as a wash liquor for the crystal mass present on the rotating drum filter. The bottoms stream from the distillation column was recycled to the reactor where the 2,2-bis(4-hydroxyphenyl)propane is prepared.

I claim as my invention:

1. A process for the purification of a crude 2,2-bis(4-hydroxyphenyl)propane mixture prepared by condensing phenol with acetone or 2,2-dimethyl-1,3-dioxolane, said mixture being substantially free of phenol, which process comprises:
    a. dissolving the crude 2,2-bis(4-hydroxyphenyl)propane and impurities in a polyhydroxy solvent selected from alkane diols and alkane triols;
    b. contacting the polyhydroxy solvent-crude 2,2-bis(4-hydroxyphenyl)propane solution with water and an ether selected from the group consisting of diethyl ether, ethyl-*n*-propyl ether, ethylisopropyl ether, methyl-tert-butyl ether, di-*n*-propyl ether, diisopropyl ether and furan, wherein said ether extracts the 2,2-bis(4-hydroxyphenyl)propane;
    c. separating the ether-2,2-bis(4-hydroxyphenyl)propane extract;
    d. distilling the ether-2,2-bis(4-hydroxyphenyl)propane extract in a column and in the presence of toluene and recovering as bottoms product a toluene-2,2-bis(4-hydroxyphenyl)propane solution;
    e. cooling the toluene-2,2-bis(4-hydroxyphenyl)propane bottoms product to form a purified 2,2-bis(4-hydroxyphenyl)propane precipitate; and
    f. recovering the purified 2,2-bis(4-hydroxyphenyl)propane.

2. The process according to claim 1 wherein the weight ratio of polyhydroxy solvent to crude 2,2-bis(4-hydroxyphenyl)propane in step 1(a) is between about 80:20 and about 75:25; the weight ratio of ether is 2,2-bis(4-hydroxyphenyl)propane in step 1(b) is between about 1:5 and about 10:1; the weight ratio of water to polyhydroxy solvent in step 1(b) is between about 40:60 and about 90:10; and the weight ratio of toluene to 2,2-bis(4-hydroxyphenyl)propane in step 1(d) is between about 3:2 and about 5:2.

3. The process according to claim 2 wherein the polyhydroxy solvent is ethylene glycol and the ether is diisopropyl ether.

4. The process according to claim 3 wherein the polyhydroxy solvent-crude 2,2-bis(4-hydroxyphenyl)-propane solution is contacted with water and an ether at a temperature of between about 30°C and about 50°C.

5. The process according to claim 4 wherein the toluene-2,2-bis(4-hydroxyphenyl)propane solution obtained as a bottoms product in step 1(d) has a temperature of between about 100° and about 130°C and wherein said toluene-2,2-bis(4-hydroxyphenyl)propane solution is cooled to a temperature of between about 40°C and about 80°C to form a purified 2,2-bis(4-hydroxyphenyl)propane precipitate.

* * * * *